United States Patent
Andersson et al.

(10) Patent No.: US 6,212,442 B1
(45) Date of Patent: Apr. 3, 2001

(54) COMPRESSING DEVICE IN ASSOCIATION WITH A DENTAL PRODUCT OR OTHER PRODUCT RELATED TO THE HUMAN BODY, OR TOOL FOR THIS PRODUCT

(75) Inventors: Matts Andersson, Lerum; Magnus Persson, Vänersborg, both of (SE)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/077,457
(22) PCT Filed: Dec. 3, 1996
(86) PCT No.: PCT/SE96/01589
§ 371 Date: Aug. 13, 1998
§ 102(e) Date: Aug. 13, 1998
(87) PCT Pub. No.: WO97/21156
PCT Pub. Date: Jun. 12, 1997

(30) Foreign Application Priority Data

Dec. 5, 1995 (SE) .................................................. 9504339

(51) Int. Cl.$^7$ ................................................ G06F 19/00
(52) U.S. Cl. ............................................. 700/194; 700/161
(58) Field of Search .................................. 700/161, 163, 700/194, 195

(56) References Cited

U.S. PATENT DOCUMENTS

| | | | |
|---|---|---|---|
| 4,575,805 | * 3/1986 | Moermann et al. | 700/163 |
| 4,611,288 | * 9/1986 | Duret et al. | 700/163 |
| 4,997,369 | 3/1991 | Shafir | 433/72 |
| 5,056,204 | * 10/1991 | Bartschi | 29/826.21 |
| 5,274,563 | * 12/1993 | Matsuura et al. | 700/161 |
| 5,334,918 | * 8/1994 | McMurty et al. | 318/568.16 |
| 5,452,219 | * 9/1995 | Dehoff et al. | 700/163 |
| 5,497,336 | 3/1996 | Andersson et al. | 700/161 |
| 5,539,649 | * 7/1996 | Walsh et al. | 700/163 |
| 5,543,103 | * 8/1996 | Hogan et al. | 264/219 |

FOREIGN PATENT DOCUMENTS 0 455 855 A1   11/1991   (EP) .

* cited by examiner

Primary Examiner—William Grant
Assistant Examiner—Chad Rapp
(74) Attorney, Agent, or Firm—Pollock, Vande Sande & Amernick, R.L.L.P.

(57) ABSTRACT

A device for compressing information sensed from a model of a product is provided. The compressed quantity of information is a subset of the control information that can be transferred, by way of a data link, to machining equipment used to make the product from a blank. The device senses the model in a first coordinate system and converts the sensed first coordinates into corresponding second coordinates, describing the shape in a second coordinate system. These second coordinates form the basis for the control information. Compressing the information substantially reduces the amount of data transmitted over a public telecommunication network of the data link.

12 Claims, 3 Drawing Sheets

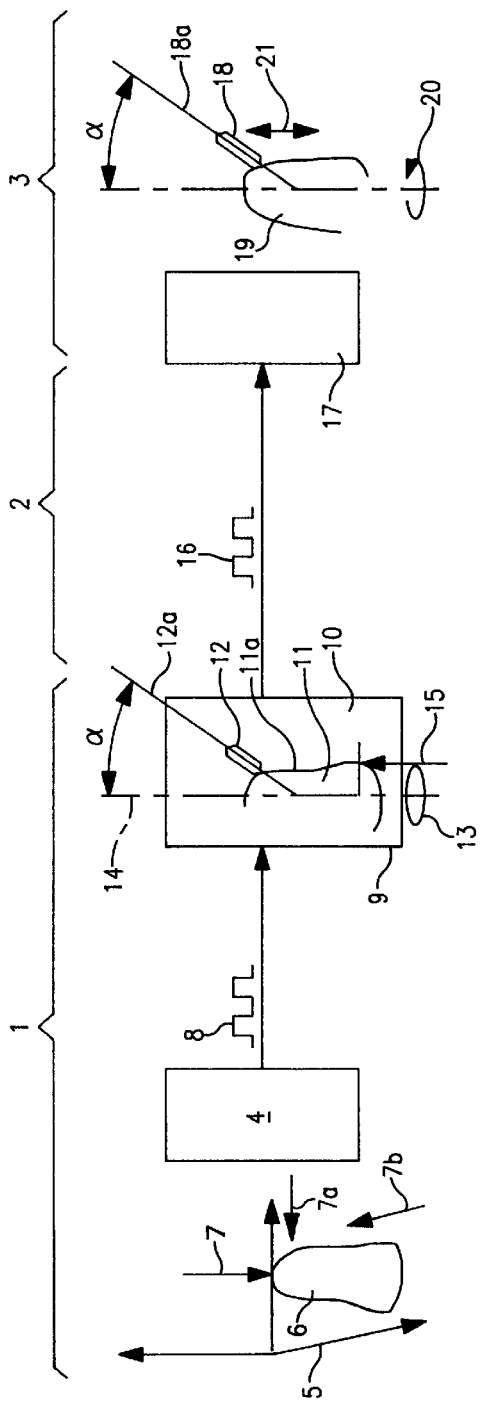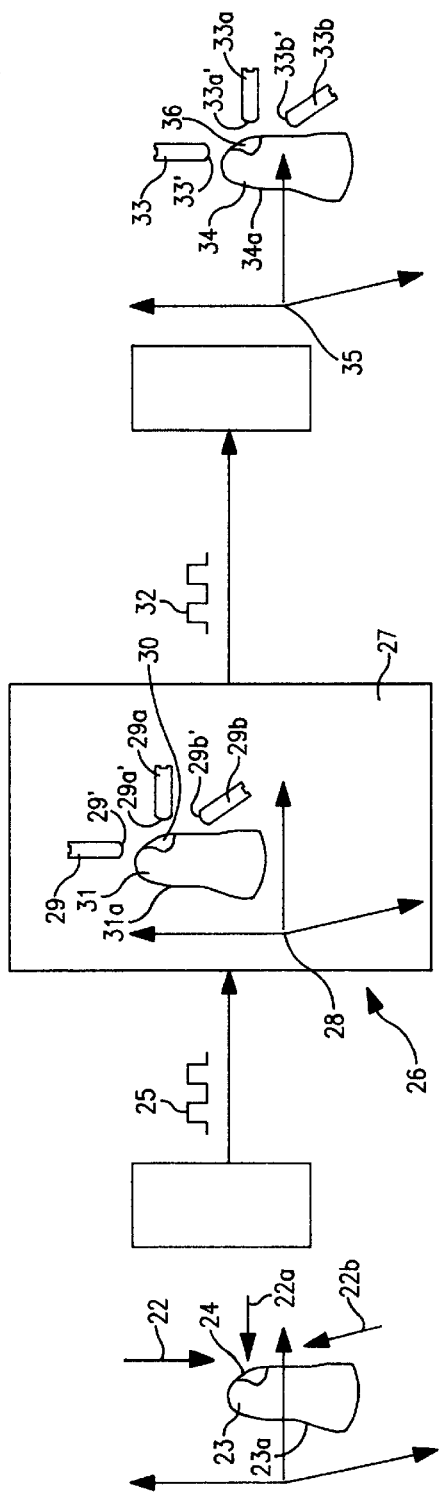

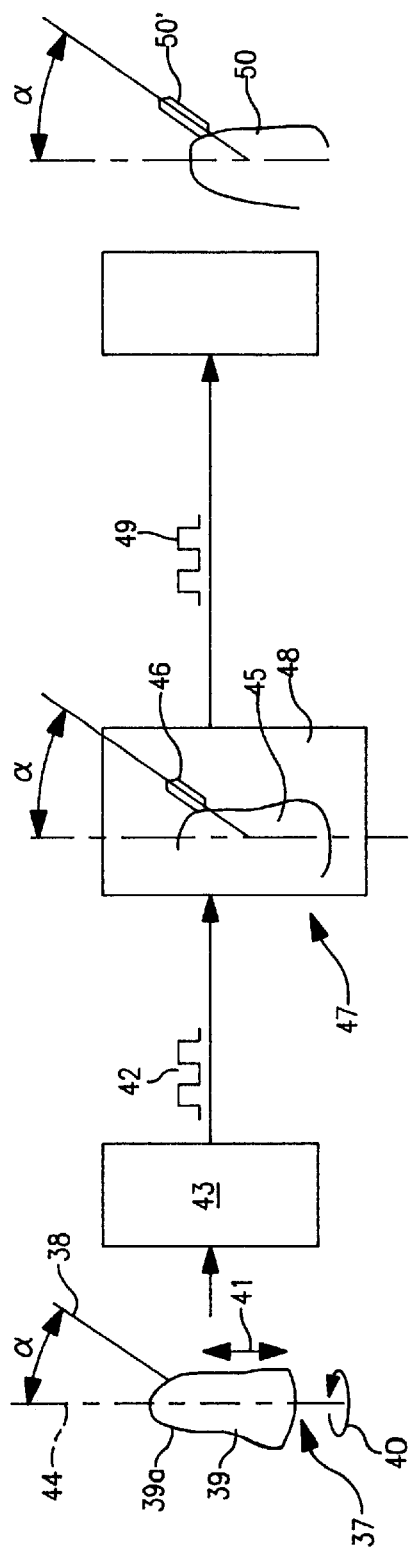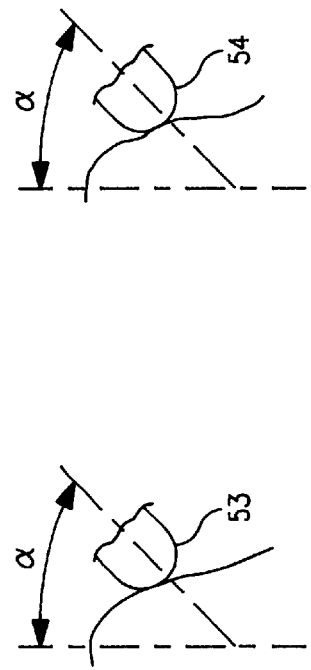

Figure 7:
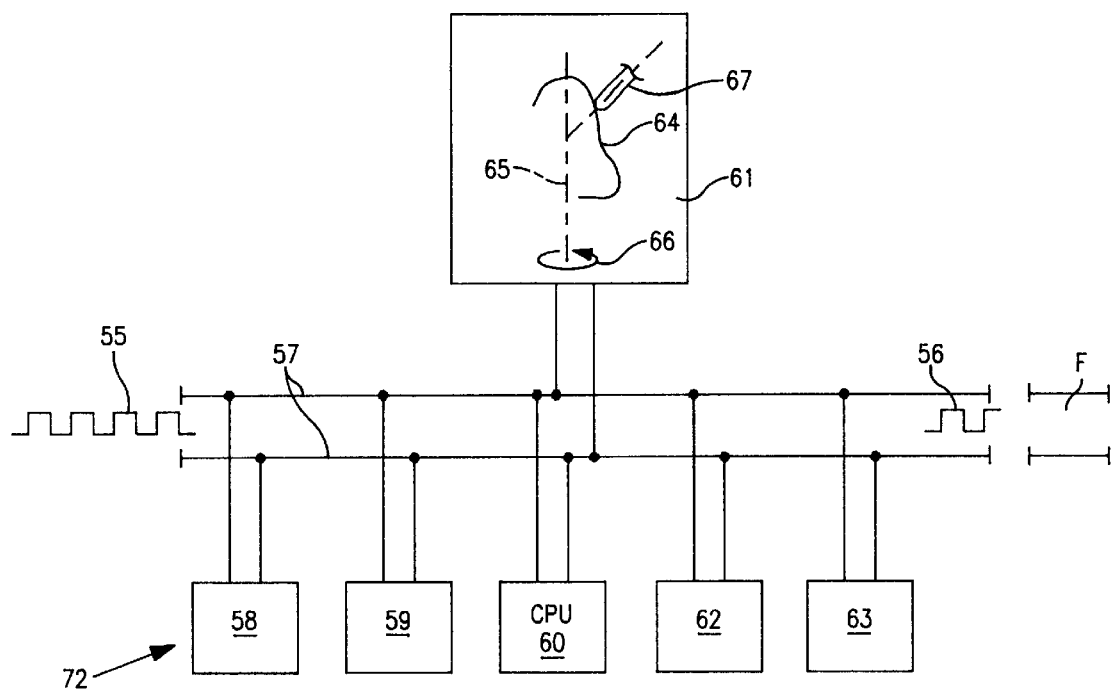

COMPRESSING DEVICE IN ASSOCIATION WITH A DENTAL PRODUCT OR OTHER PRODUCT RELATED TO THE HUMAN BODY, OR TOOL FOR THIS PRODUCT

TECHNICAL FIELD

The present invention relates to a device for compressing the quantity of information which is obtained in an apparatus for sensing or reading even the complex shape of a model of a dental product or other product related to the human body, or body part, or tool for producing the product or the body part. The compressed quantity of digital information is included in, or forms, control information, which can be transferred by way of a remote link and/or data link, for machining equipment which is arranged in or at premises which are separate from the locality for the sensing or reading. With the aid of the control information, the machining equipment produces, from a blank, the said product, a replacement part for the said body part, or the tool.

STATE OF THE ART

It is previously known, in connection with producing dental products, to carry out a sensing function in both the cartesian and the polar coordinate systems. In this context, it is known that the sensing in, for example, the cartesian coordinate system normally results in large quantities of information.

It is also previously known to utilize the same profiles on a mechanical sensing needle and a tool in the machining equipment in question, which contributes to reducing the quantity of information. As far as the quantity of information which has to be transferred from a sensing unit to a machining unit is concerned, this approach is advantageous when, in the sensing and the machining functions, the model and the sensing needle, and the blank and the tool, respectively, are also rotated and displaced longitudinally in a reciprocal manner and when the same inclinations (45°) between the model and the sensing needle, and the blank and the tool, respectively, are retained.

It is also known that non-mechanical sensing principles, for example optical sensing principles, increase the quantity of information.

It is also previously known to transfer the sensed information from a sensing unit to the machining unit, for the purpose of achieving control information for the latter, on a telecommunication link, for example an established link in the public telecommunication network.

Reference is also made to EP 541500 A1.

ACCOUNT OF THE INVENTION

TECHNICAL PROBLEM

In some cases, there is a need to be able to carry out reading or sensing functions using systems and equipment which yield a relatively large quantity of read-off or sensed information, which quantity can only be handled inefficiently in association with transferring it via the remote and/or data link. In these cases, it is a matter of importance that it should be possible to compress the quantity of information before the transmission to the machining unit takes place without essential machining information being lost for that reason. In this context, it can be noted that the demands on manufacturing precision are high (for example 0.02 mm) in the case of dental products and compressions cannot be permitted which distort the reading. The compression must be carried out in such a way that the characteristics, and complex, individual shape, of the model or equivalent are transferred to the product, tool, etc., which is produced. In addition, quantities of information which give rise to long transfer times on the link are unacceptable. It is only possible to permit transfer times on the link of at most a few minutes. Consequently, there is a need to compress the reading substantially in the case of reading systems which yield large quantities of information. The invention is directed towards solving this problem.

There is a need to reduce the quantity of information, prior to transmission on the link, in the case of, for example, sensing a model, body part (tooth crown, tooth neck, oral cavity, etc.) or tool having complicated internal or external shapes and which is sensed in the cartesian coordinate system. The invention solves this problem as well.

There is also a need to employ non-mechanical principles using light (laser), sound, etc., when reading a model, for example.

An efficient machining function can be achieved by working in the polar coordinate system, where the blank is rotated and the blank and the tool are simultaneously displaced longitudinally in a reciprocal manner, with the inclination between the tool and the blank preferably being selected to be 45°. It should be possible to maintain the arrangement in question despite the reading taking place in a cartesian coordinate system. The invention solves this problem as well.

SOLUTION

A presently proposed device which solves the abovementioned problems can principally be regarded as being characterized in that the compression can be effected by means of the apparatus sensing or reading the model or the body part in a first (for example cartesian) coordinate system for the purpose of extracting first coordinates which can be assigned to this system. In this context, first means are organized for converting the first coordinates which have been obtained in this way to corresponding second coordinates which describe the shape in a second, or polar, coordinate system. The second coordinates form or constitute the basis for the control information.

The new device can also be regarded as being characterized in that second means are supplied information which corresponds to, and is essentially proportional to, a size of a surface by which a tool, for example in the form of a milling cutter, which is included in the machining equipment interacts with the blank when the latter is being machined. In this context, it is characteristic that the said surface size is at least $\frac{1}{10}$–$\frac{1}{100}$ of the surface of the model, body part or tool. Using the said supplied information, the second means reduce the sensing or reading information in dependence on the surface size such that there is a more extensive reduction in the case of a larger surface size, and vice versa.

The new device can also be regarded as being characterized in that the apparatus senses the model or the body part in a first (polar) or second (cartesian) coordinate system in accordance with a non-mechanical (i.e. optical, sound-related, etc.) sensing or reading principle. In this context, third means are arranged to convert the non-mechanical sensing or reading function to a mechanical sensing function which operates with a sensing element which interacts with the shape of the model/replacement part/tool. In this context, the profile of the sensing element which interacts with the shape, and the inclination of the sensing element in relation to the shape, correspond to the profile of a tool part which interacts with the blank or, respectively, the inclination of the tool in relation to the blank.

In one embodiment of the invention concept, the said first or second means include a computer which can be used to simulate both the sensed or read-off shape of the model or body part and a profile which corresponds to the profile of the part of the machining tool which can interact with the blank. In a further embodiment, the first means activate the computer to simulate rotation, around a central axis, of the sensed or read-off model, body part or tool. In a supplementary, or alternative, manner, the computer simulates a sensing function, effected in the polar coordinate system, relative to the surface presentation of the model, body part or tool by means of a profile which bears against the shape or surface of the model, body part or tool and which corresponds to the profile of the tool of the machining equipment. In this context, the first means read the second coordinates, in a manner known per se, using the sensing and reading function and the simulated reciprocal movements of the model/body part/tool in order to obtain the control information.

In a further embodiment, the second means activate the computer to simulate, in a cartesian coordinate system, the movements of the sensing function in relation to the read-off or sensed surface of the simulated model/body part/tool in different sensing positions and to indicate respective second coordinates when there is interaction, in each sensing position, between the sensed shape and a sensing profile which corresponds to the profile of the tool of the machining equipment.

The third means also include a computer which can be used to simulate the mechanical sensing principle with the aid of information which is obtained when reading by means of a non-mechanical sensing principle.

The said simulations can be reproducible on the screen of the computer. The simulations can also be effected on the basis of values which are recorded in tables, data files or equivalent in association with reading or sensing the model/body part/tool, or on the basis of first or second coordinates in memory elements which are included in the computer.

As far as the cartesian coordinate system is concerned, a number of sets of second coordinates are obtained in each sensing position, which coordinates are situated within, or represent, a sensing surface of the profile in the simulated sensing function, which sensing surface corresponds to the surface of the tool which can interact with the blank. A single set of the second coordinates represents the surface contact which is effected between the simulated sensing profile and the simulated shape of the part, body part or tool in each sensing position. The second means reduce or disregard the remaining second coordinates in the coordinate set in question, thereby reducing or compressing the quantity of information. The first and second means include programs or software which participate in extracting the first or second coordinates. In association with this, use can also be made of conventional programs which compress quantities of data information.

ADVANTAGES

By means of that which has been proposed above, machining equipment which works with small quantities of information but is nevertheless accurate can be made to interact, by way of a remote link and/or data link, with reading functions which per se yield large quantities of information. The link does not have to be occupied for unacceptably long periods of time. The device enables transfer to take place between two different coordinate systems and facilitates the overall construction of the reading system and machining system. The freedom of choice with regard to the sensing principle is extensive, and optics, laser, sound, mechanics, capacitance, etc., can be employed in the invention as sensing means. Requisite high degrees of accuracy can be retained during the manufacture despite the compression functions. Tried and tested components and equipment can be used in the manufacture in question, which should also be possible using materials which are as hard as titanium.

FIGURE DESCRIPTION

Figure 8:
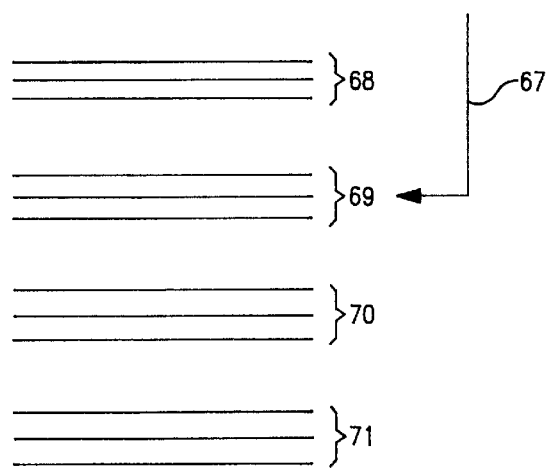

A presently proposed embodiment of a device which exhibits the characteristics which are significant for the invention will be described below while at the same time referring to the attached drawings, where FIG. 1 shows, in diagrammatic form, sensing, simulating and machining functions for a first instance of sensing and machining, FIG. 2 shows, in diagrammatic form, the corresponding functions in a second instance of sensing and machining, FIG. 3 shows, in diagrammatic form, the corresponding functions in a third instance of machining, FIG. 4 shows the principle of the sensing function using optics, FIG. 5 shows the principle of a simulated mechanical sensing function, FIG. 6 shows the principle of machining between a blank and a tool, FIG. 7 shows, in block diagram form, the assembly of the respective means, FIG. 8 shows the principle for designating coordinate sets.

DETAILED EMBODIMENT

FIG. 1 shows a reading unit or reading site, indicated by 1, a transfer link in a remote network and/or data network, indicated by 2, and a machining place or machining locality, indicated by 3. This division of the reading, transfer and machining functions is previously known. At the reading site, for example in a dental technician's laboratory, a reading apparatus is symbolized by 4. The apparatus operates in a first (for example cartesian) coordinate system 5, in which a model 6 is placed. The reading principle is assumed to constitute a non-mechanical principle and can consist of a known optical reading function which operates with sound, etc., which reading function is symbolized by the arrow 7. A rather extensive quantity of digital information 8, depending on the reading function, is obtained from the apparatus 4. The latter quantity of information is supplied to a first means 9, which can include, or consist of, a computer, for example a PC computer, which is indicated symbolically. Using the quantity of information 8, the model 6 is simulated in the computer, where the simulated model has been indicated by 11. The computer also simulates a mechanical sensing function which includes a sensing needle (for example having a spherical shape) or a sensing element 12, which, during the sensing, can bear against, and interact with, the shape 11a of the model. The shape of the sensing needle corresponds to the shape of the tool which is described below (cf. 18). The means 9, or the computer, can also simulate a rotation 13 of the model 11 around its longitudinal axis 14. The means, or the computer, also simulates reciprocal displacement movements 15 between the sensing element 12 and the model 11. The sensing will thus be characterized by the fact that the simulated model 11 is rotated and reciprocal longitudinal displacement movements 15 are applied to the sensing element and/or the model 11. The longitudinal axes 12a of the sensing element is inclined to the longitudinal axis 14 of the model by an angle α. A quantity of information 16, which is essentially reduced in relation to the quantity of the information 8, is obtained in this way from the means 9, or the computer 10, by means of sensing and extracting signals during the simulated sensing. The reduced quantity of information can be employed as control information for the machining equipment 17 at the site 3. The machining equipment includes a tool part (milling cutter) 18, which interacts with blank 19. The longitudinal axis 18a of the tool part 18 exhibits an angle α which corresponds to the abovementioned angle α. The blank 19 is also rotated in a rotational direction 20 and the tool can be guided vertically relative to the blank in the vertical direction 21. The profiles of the sensing element 12 and the tool 18 essentially correspond to each other as described above. In this context, the number of positions which are sensed per revolution and the lead of the reciprocal movements of the sensing needle and the model are important and the movements which have occurred reciprocally between the needle and the model should essentially correspond to the movements between the tool and the blank, i.e. 13/15=20/21. By means of the described analogy between the simulated model and the sensing needle, and the blank and the tool part, it is possible to achieve a very precise copying function at the machining place despite the quantity of information 16 having been substantially reduced. The sensing function in the Cartesian system on the reading side can be carried out in a manner know per se by sensing the coordinates in the direction 7, 7a and 7b.

In FIG. 2, the reading takes place in a corresponding manner in a cartersian coordinate system. A spherical coordinate system, a cylindrical coordinate system, etc., can be used as an alternative to this system. A surface 24 has been indicated on the read-off model or tool part 23. When reading is carried out using optics, laser, etc., a large number of coordinate readings are obtained for this surface 24, as are obtained for the remainder of the shape 23a of the model. This results in a large quantity of information 25 with regard to the read-off shape 23a. Other means 26 which include, or consist of, a computer 27, for example a PC computer. The second means 26, or the computer 27, can simulate the cartesian reading system 28 in question. In this case, use is made of a mechanical sensing which has been represented by sensing elements 29, 29a and 29b which are directed towards a surface 30, corresponding to the surface 24, on the simulated model 31. The respective sensing elements exhibit profiles 29', 29a' and 29b' which can interact with the model. Each profile is of an order of size which, when interacting with the outer surface 31a of the model 31, describes the surface 30 in question. In the simulated case, only one coordinate set, namely the coordinate set which first indicates contact between the sensing element 29 and the surface 31a, will be selected from the coordinate sets which are included in the quantity of information 25 and which represent the surface 24. Remaining coordinate sets are eliminated or discriminated against by the means 26 or the computer 27. This thereby substantially reduces the quantity of information 25. The reduced quantity is symbolized by 32. Tool parts 33, 33a and 33b, which correspond to the sensing elements 29, 29a and 29b and which have the shapes 33'. 33a' and 33b' on their front parts, have been shown at the machining unit. In addition, the tool parts are attacking the blank 34 in a manner corresponding to that with which the sensing elements are attacking the simulated model 31. The blank 34 is arranged in its cartersian system 35 in a manner corresponding to that of the model in its cartesian system 28. In conformity with the concept of the invention, the surfaces 24, 30 and 36 constitute at least $\frac{1}{10}$–$\frac{1}{1000}$ of the total surface 23a, 31a and 34a, respectively. In this way, it is possible for the quantity of information 25 to be reduced substantially to the quantity of information 32.

In the instance shown in FIG. 3, the sensing takes place in the polar coordinate system 37 or another selected coordinate system. A non-mechanical sensing principle is symbolized by 38 and the sensed model 39 is rotated in the direction of rotation 40 and reciprocal height movements 41 are effected between the sensing function 38 (the sensing beam) and the model 39, with the sensing sensing the outer shape 39a of the model. This sensing principle also yields a large quantity of information 42 from the sensing system 43, despite the angle between the sensing beam and the longitudinal axis 44 of the model 39 being as great as the angles α for the simulated model 45 and the simulated sensing element 46 and between the blank 50 and the tool 50', respectively. In this instance, simulation takes place in third means 47 which include, or consist of, the computer 48, the model 45 and the sensing element, in a manner corresponding to the embodiment shown in FIG. 1. The machining unit also has a corresponding design and operates in accordance with operational principles which correspond to those of the instance shown in FIG. 1.

FIG. 4 shows an optical sensing principle diagrammatically by means of 51. The outer shape 52a of the model 52 is sensed by the model 52 being rotated and the sensing element 51 and the model being displaced vertically relative to each other, cf. above. FIGS. 5 and 6 show, in magnified form, the similarities in the profiles 53 and 54, respectively, of the sensing element and the tool, respectively. The inclination angles α are also indicated.

FIG. 7 shows an example of how compression of a large quantity of incoming information 55 to a substantially reduced quantity of information 56 is arranged to take place. A bus link for receiving the quantity of information 55 is indicated by 57. The equipment includes memory elements 58 and 59 in which the incoming quantity of information can be stored in a manner known per se. A CPU 60 is also included. A screen 61 is also connected to the bus link. A working memory is indicated by 62 and outgoing matching circuits by 63. Using software, the microcomputer 60 can collect the information which is stored in memories 58 and 59 and simulate the sensed shape 64 in question on the screen, which shape can, as described above, be rotated around the axis 65 in a direction of rotation 66. The sensing element 67 can also be simulated both as regards its appearance and as regards its inclination relative to the surface 64, as described above. As described above, the shape of the sensing element is given a design which corresponds to the shape of the tool in question, which has been programmed into the memories 58 and 59. By means of sensing, in a manner known per se, the longitudinal displacement movements of the sensing elements 67 relative to the surface 64, information about the simulated shape or the surface can be obtained and stored in the memory 62, or another memory. Using the abovementioned similarity to the tool in the machining equipment, the information stored in memory 62 becomes substantially reduced as compared with the incoming information. The reduced information 56 can be transmitted, by means of the matching circuit 63, on the established telecommunications line F in question. The circuit 63 includes a modem, calling equipment, etc. No simulation needs to take place on screen 61, and, instead, the simulation can be performed directly on the information which has been entered in memories 58 and 59, which information is thereby arranged into tables, files, etc. The addressing functions are previously known per se and will not be described here. With reference to the embodiments shown in FIG. 8, the designating function 67 can be employed for a number of coordinate sets 68, 69, 70 and 71, which represent the coordinate sets within the sensed surface 24 in FIG. 2. Only one coordinate set is to be designated, and coordinate set 69 has been designated in the present instance. In one exemplary embodiment, information relating to the surface size 24 in FIG. 2 is entered in, for example, the memory element 72. Reference is also made to other compression principles, cf., e.g., EP 541500 A1.

The invention is not limited to the embodiment which has been shown above by way of example, and can be modified within the scope of the subsequent patent claims and the invention concept.

What is claimed is:

1. Device for compressing the quantity of information which is obtained in an apparatus for sensing information from a model of a product, with the compressed quantity of information being a subset of the control information, which can be transferred by way of a data link, to machining equipment used to make the product from a blank;

the apparatus senses the model in a first coordinate system, for the purpose of extracting first coordinates which can be assigned to this system, and a first means is arranged to convert the first coordinates, which have been obtained in this way, into corresponding second coordinates which describe the shape in a second coordinate system, which second coordinates form or constitute the basis for the control information; and the data link comprises a public telecommunication network, wherein the compression substantially reduces the amount of information obtained from the model before transmitting the information over the data link and the compression is affected by means of at least one of the following:

a) second means being supplied information which represents, and has a quantity that is essentially proportional to a size on a surface by which a tool, which is included in the machining equipment, interacts with the blank when the latter is being machined, surface size is at least $\frac{1}{10}$–$\frac{1}{100}$ of the surface of the model, and the second means reduces with the aid of the supplied information, the sensing information in dependence on the surface size so that a greater reduction occurs with a larger surface size and vice versa; and b) the apparatus senses the model in either the first or second coordinate systems in accordance with a non-mechanical sensing principle and third means converts the non-mechanical sensing function to a mechanical sensing function and uses a sensing element to interact with the simulated shape such that the sensing element's profile and inclination, in relation to the simulated shape corresponds to the profile and inclination of the part of a tool which interacts with the blank.

2. Device according to claim 1, wherein said first and second means, respectively, include a computer which can simulate the sensed shape of the model as a profile, which profile corresponds to the profile of the part of the machining tool which can interact with the blank.

3. Device for compressing the quantity of information which is obtained in an apparatus for sensing information from a model of a product, with the compressed quantity of information being a subset of the control information, which can be transferred by way of a data link, to machining equipment used to make the product from a blank;

the apparatus senses the model in a first coordinate system, for the purpose of extracting first coordinates which can be assigned to this system, and a first means is arranged to convert the first coordinates, which have been obtained in this way, into corresponding second coordinates which describe the shape in a second coordinate system, which second coordinates form or constitute the basis for the control information;

the data link comprises a public telecommunication network, wherein the compression substantially reduces the amount of information obtained from the model before transmitting the information over the data link and the compression is affected by means of at least one of the following:

a) second means being supplied information which represents, and has a quantity that is essentially proportional to, a size on a surface by which a tool, which is included in the machining equipment, interacts with the blank when the latter is being machined, the surface size is at least $\frac{1}{10}$–$\frac{1}{100}$ of the surface of the model, and the second means reduces, with the aid of the supplied information, the sensing information in dependence on the surface size so that a greater reduction occurs with a larger surface size and vice versa; and b) the apparatus senses the model in either the first or second coordinate systems in accordance with a non-mechanical sensing principle and third means converts the non-mechanical sensing function to a mechanical sensing function and uses a sensing element to interact with the simulated shape such that the sensing element's profile and inclination, in relation to said simulated shape corresponds to the profile and inclination of the part of a tool which interacts with the blank;

the first and second means, respectively, include a computer which can simulate the sensed shape of the model as a profile, which profile corresponds to the profile of the part of the machining tool which can interact with the blank; and the first means activates the computer to simulate rotation, around its own central axis, of the sensed model and simulate a sensing function, which is affected in a polar system, relative to the vertical direction of the model, by means of a profile which bears against the surface shape of the model and which corresponds to the profile of the tool of the machining equipment, with the first means reading the second coordinates with the aid of the sensing function and the simulated reciprocal movements of the model, for the purpose of obtaining the control information.

4. Device for compressing the quantity of information which is obtained in an apparatus for sensing information from a model of a product, with the compressed quantity of information being a subset of the control information, which can be transferred by way of a data link, to machining equipment used to make the product from a blank;

the apparatus senses the model in a first coordinate system, for the purpose of extracting first coordinates which can be assigned to this system, and a first means is arranged to convert the first coordinates, which have been obtained in this way, into corresponding second coordinates which describe the shape in a second coordinate system, which second coordinates form or constitute the basis for the control information;

the data link comprises a public telecommunication network, wherein the compression substantially reduces the amount of information obtained from the model before transmitting the information over the data link and the compression is affected by means of at least one of the following:

a) second means being supplied information which represents and has a quantity that is essentially proportional to, a size on a surface by which a tool, which is included in the machining equipment, interacts with the blank when the latter is being machined, the surface size is at least $\frac{1}{10}$–$\frac{1}{100}$ of the surface of the model, and the second means reduces, with the aid of the supplied information, the sensing information in dependence on the surface size so that a greater reduction occurs with a larger surface size and vice versa; and b) the apparatus senses the model in either the first or second coordinate systems in accordance with a non-mechanical sensing principle and third means converts the non-mechanical sensing function to a mechanical sensing function and uses a sensing element to interact with the simulated shape such that the sensing element's profile and inclination, in relation to said simulated shape corresponds to the profile and inclination of the part of a tool which interacts with the blank;

the first and second means, respectively, include a computer which can simulate the sensed shape of the model as a profile, which profile corresponds to the profile of the part of the machining tool which can interact with the blank; and the second means activates the computer to simulate, in a selected coordinate system, the movements of a sensing function in relation to the sensed surface of the simulated model, in different sensing positions, and to specify respective second coordinates when interaction occurs, in each sensing position, between the sensed shape and a sensing profile which corresponds to the profile of the tool of the machining equipment.

5. Device for compressing the quantity of information which is obtained in an apparatus for sensing information from a model of a product, with the compressed quantity of information being a subset of the control information, which can be transferred by way of a data link, to machining equipment used to make the product from a blank;

the apparatus senses the model in a first coordinate system, for the purpose of extracting first coordinates which can be assigned to this system, and a first means is arranged to convert the first coordinates, which have been obtained in this way, into corresponding second coordinates which describe the shape in a second coordinate system, which second coordinates form or constitute the basis for the control information;

the data link comprises a public telecommunication network, wherein the compression substantially reduces the amount of information obtained from the model before transmitting the information over the data link and the compression is affected by means of at least one of the following:

a) second means being supplied information which represents, and has a quantity that is essentially proportional to, a size on a surface by which a tool, which is included in the machining equipment, interacts with the blank when the latter is being machined, the surface size is at least $\frac{1}{10}$–$\frac{1}{100}$ of the surface of the model, and the second means reduces, with the aid of the supplied information, the sensing information in dependence on the surface size so that a greater reduction occurs with a larger surface size and vice versa; and b) the apparatus senses the model in either the first or second coordinate systems in accordance with a non-mechanical sensing principle and third means converts the non-mechanical sensing function to a mechanical sensing function and uses a sensing element to interact with the simulated shape such that the sensing element's profile and inclination, in relation to said simulated shape corresponds to the profile and inclination of the part of a tool which interacts with the blank; and the third means includes a computer, which can simulate the mechanical principle.

6. Device according to claim 2, wherein each simulation can be reproduced on the screen of the computer.

7. Device according to claim 2, wherein the simulations can be affected on values of first or second coordinates in memory elements, which are included in the computer, which values were entered in data structures in association with sensing the model.

8. Device for compressing the quantity of information which is obtained in an apparatus for sensing information from a model of a product, with the compressed quantity of information being a subset of the control information, which can be transferred by way of a data link, to machining equipment used to make the product from a blank;

the apparatus senses the model in a first coordinate system, for the purpose of extracting first coordinates which can be assigned to this system, and a first means is arranged to convert the first coordinates, which have been obtained in this way, into corresponding second coordinates which describe the shape in a second coordinate system, which second coordinates form or constitute the basis for the control information;

the data link comprises a public telecommunication network, wherein the compression substantially reduces the amount of information obtained from the model before transmitting the information over the data link and the compression is affected by means of at least one of the following:

a) second means being supplied information which represents, and has a quantity that is essentially proportional to, a size on a surface by which a tool, which is included in the machining equipment, interacts with the blank when the latter is being machined, the surface size is at least $\frac{1}{10}$–$\frac{1}{100}$ of the surface of the model, and the second means reduces, with the aid of the supplied information, the sensing information in dependence on the surface size so that a greater reduction occurs with a larger surface size and vice versa; and b) the apparatus senses the model in either the first or second coordinate systems in accordance with a non-mechanical sensing principle and third means converts the non-mechanical sensing function to a mechanical sensing function and uses a sensing element to interact with the simulated shape such that the sensing element's profile and inclination, in relation to said simulated shape corresponds to the profile and inclination of the part of a tool which interacts with the blank;

the first and second means, respectively, include a computer which can simulate the sensed shape of the model as a profile, which profile corresponds to the profile of the part of the machining tool which can interact with the blank; and a number of sets of second coordinates, which are situated within a sensing surface on the profile in the simulated sensing function, which sensing surface corresponds to the surface of the tool which can interact with the blank, belong to each sensing position in the selected coordinate system, and a set of the second coordinates represents the surface contact which is affected between the simulated sensing profile and the shape of the simulated part in each sensing position, with the second means reducing the remaining second coordinates in the coordinate set in question and in this way affecting the compression of the quantity of information.

9. Device for compressing the quantity of information which is obtained in an apparatus for sensing information from a model of a product, with the compressed quantity of information being a subset of the control information, which can be transferred by way of a data link, to machining equipment used to make the product from a blank;

the apparatus senses the model in a first coordinate system, for the purpose of extracting first coordinates which can be assigned to this system, and a first means is arranged to convert the first coordinates, which have been obtained in this way, into corresponding second coordinates which describe the shape in a second coordinate system, which second coordinates form or constitute the basis for the control information;

the data link comprises a public telecommunication network, wherein the compression substantially reduces the amount of information obtained from the model before transmitting the information over the data link and the compression is affected by means of at least one of the following:

a) second means being supplied information which represents, and has a quantity that is essentially proportional to, a size on a surface by which a tool, which is included in the machining equipment, interacts with the blank when the latter is being machined, the surface size is at least $1/10$–$1/100$ of the surface of the model, and the second means reduces, with the aid of the supplied information, the sensing information in dependence on the surface size so that a greater reduction occurs with a larger surface size and vice versa; and b) the apparatus senses the model in either the first or second coordinate systems in accordance with a non-mechanical sensing principle and third means converts the non-mechanical sensing function to a mechanical sensing function and uses a sensing element to interact with the simulated shape such that the sensing element's profile and inclination, in relation to said simulated shape corresponds to the profile and inclination of the part of a tool which interacts with the blank; and any one of the first, second or third means includes software which cooperates in extracting one of the first or second coordinates.

10. Device for compressing the quantity of information which is obtained in an apparatus for sensing information from a model of a product, with the compressed quantity of information being a subset of the control information, which can be transferred by way of a data link, to machining equipment used to make the product from a blank;

the apparatus senses the model in a first coordinate system, for the purpose of extracting first coordinates which can be assigned to this system, and a first means is arranged to convert the first coordinates, which have been obtained in this way, into corresponding second coordinates which describe the shape in a second coordinate system, which second coordinates form or constitute the basis for the control information;

the data link comprises a public telecommunication network, wherein the compression substantially reduces the amount of information obtained from the model before transmitting the information over the data link and the compression is affected by means of at least one of the following:

a) second means being supplied information which represents, and has a quantity that is essentially proportional to, a size on a surface by which a tool, which is included in the machining equipment, interacts with the blank when the latter is being machined, the surface size is at least $1/10$–$1/100$ of the surface of the model, and the second means reduces, with the aid of the supplied information, the sensing information in dependence on the surface size so that a greater reduction occurs with a larger surface size and vice versa; and b) the apparatus senses the model in either the first or second coordinate systems in accordance with a non-mechanical sensing principle and third means converts the non-mechanical sensing function to a mechanical sensing function and uses a sensing element to interact with the simulated shape such that the sensing element's profile and inclination, in relation to said simulated shape corresponds to the profile and inclination of the part of a tool which interacts with the blank; and any one of the first, second or third means also includes convention programs for compressing the quantities of data information.

11. Device according to claim 3, wherein:

each simulation can be reproduced on the screen of the computer.

12. Device according to claim 3, wherein:

the simulations can be affected on values of first or second coordinates in memory elements, which are included in the computer, which values were entered in data structures in association with sensing the model.

* * * * *